COOLED SURGICAL INSTRUMENT
Original Filed Jan. 29, 1962 2 Sheets-Sheet 1
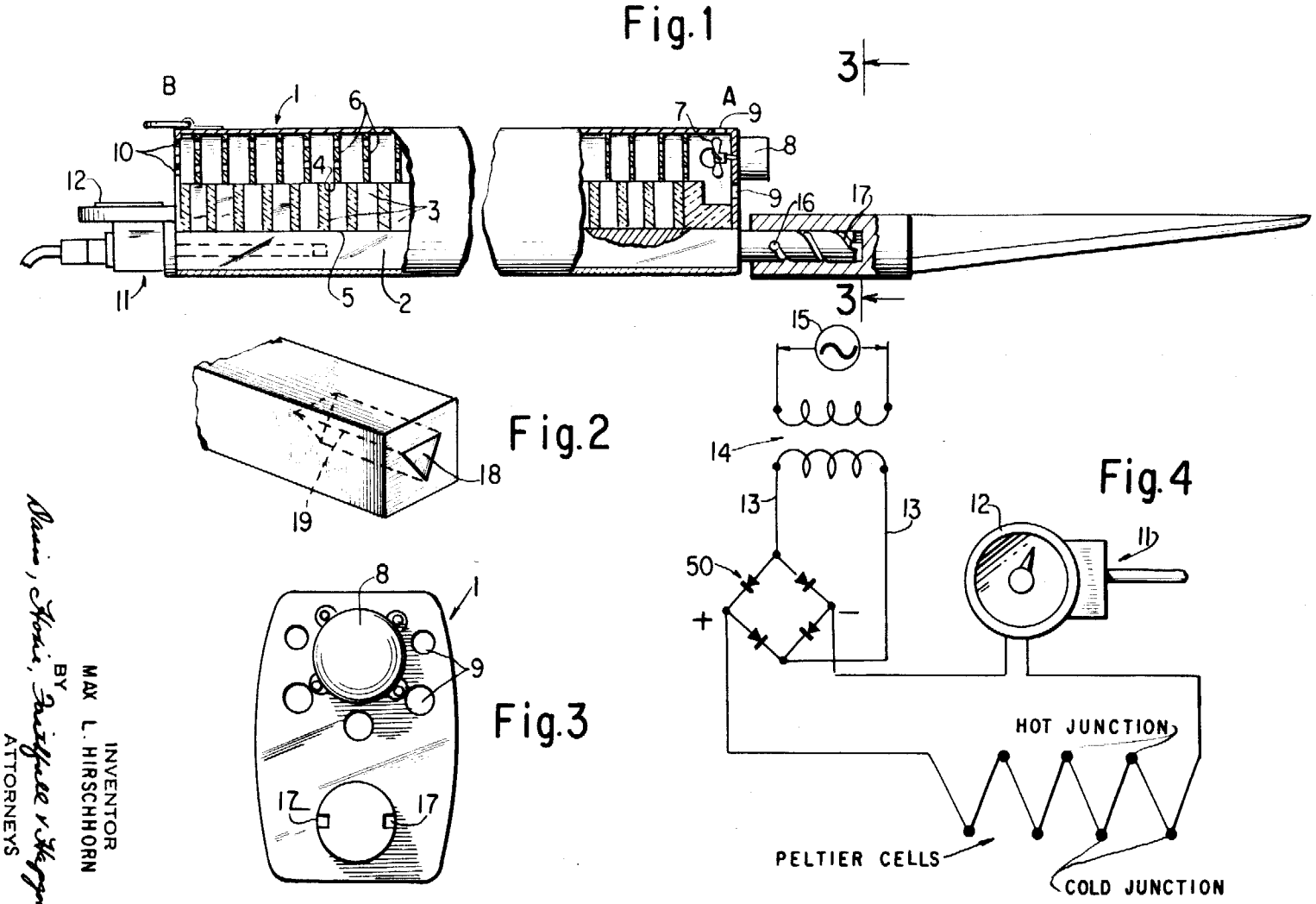
INVENTOR
MAX L. HIRSCHHORN
BY
Davis, Hoxie, Faithfull & Hapgood
ATTORNEYS Oct. 3, 1967

M. L. HIRSCHHORN

Re. 26,276

COOLED SURGICAL INSTRUMENT

Original Filed Jan. 29, 1962

2 Sheets-Sheet 2

INVENTOR
MAX L. HIRSCHHORN
BY
Davis, Hoxie, Faithfull & Hapgood
ATTORNEYS

United States Patent Office

Re. 26,276
Reissued Oct. 3, 1967

26,276
COOLED SURGICAL INSTRUMENT

Max L. Hirschhorn, 5601 13th Ave.,
Brooklyn, N.Y. 11219

Original No. 3,093,135, dated June 11, 1963, Ser. No. 169,266, Jan. 29, 1962. Application for reissue May 28, 1965, Ser. No. 463,068
7 Claims. (Cl. 128—303.1)

Matter enclosed in heavy brackets [ ] appears in the original patent but forms no part of this reissue specification; matter printed in italics indicates the additions made by reissue.

The present invention relates to surgical instruments and more particularly to a cooled surgical instrument.

At the present time surgery is performed with knives, probes, biopsy scoops and other instruments which are sterilized and then allowed to cool to room temperature. Necrotizing thermo coagulative devices are also used. Recent medical investigations have shown the value in certain operative techniques of cooling parts of the body. For example, shock and hemorrhage may be lessened in brain surgery if the blood entering the brain is cooled to approximately 60° F. by circulating it through external cooling means. In other operative techniques the entire body is cooled so as to reduce the body metabolism or ethyl chloride is sprayed on the skin to freeze it by evaporation prior to opening a draining incision.

It is an objective of the present invention to provide a surgical instrument having a cutting edge *or tool* which is considerably cooled below ambient room temperature. The cooled edge acts to lower the flow of blood, lower pain, and preserve the viability of the tissue by reducing its local metabolic needs below the shock stage.

In accordance with the present invention a surgical instrument is provided having a handle cooled by its own internal refrigerating system. A plurality of metal heat conductive surgical [instruments] *tools* may be removably inserted into the end of the handle. Preferably, the handle has an automatic temperature sensing and control apparatus so that the temperature of the surgical [instruments] *tools* may be predetermined and held constant.

Other objectives of the present invention will be apparent from the below detailed description of a preferred embodiment along with the accompanying drawings, in which:

FIGURE 1 is a side sectional view of the surgical instrument showing the internal construction of the surgical handle;

FIGURE 2 is a perspective view showing an alternative to the male end of the handle of FIGURE 1;

FIGURE 3 is a front view of the handle of FIGURE 1;

FIGURE 4 is an electrical circuit diagram of the power supply for the handle;

Figure 5:
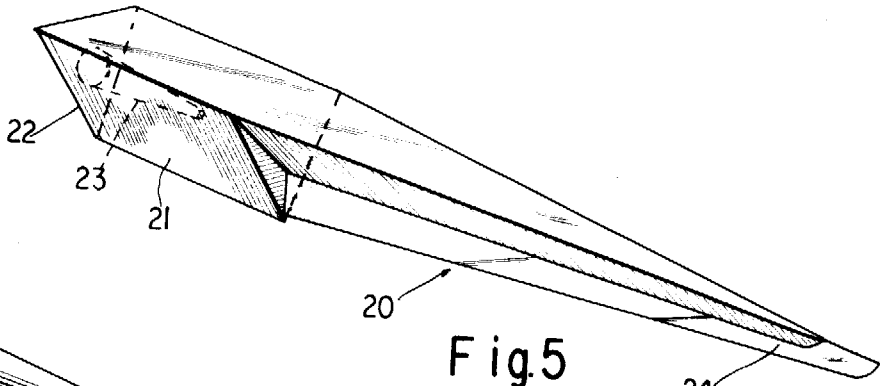
FIGURE 5 is a perspective view showing a surgical blade with its handle portion adapted to fit into the male end shown in FIGURE 2.

The surgical handle shown in FIGURE 1 consists of a body member 1 which is preferably of a heat insulative material, for example, a plastic thermosetting material such as a phenolformaldehyde resin which has low heat conductivity and may be sterilized by ordinary steam hospital sterilizing apparatus. The insulative body member 1 has within it a solid, rectangular and elongated metal heat conductive rod 2, preferably of silver, copper, or copper alloy. Situated above the rod 2 and in physical contact with it are a plurality of Peltier elements 3. The cold junction 5 of the Peltier elements are in contact with rod 2, while the hot junction 4 is directed away from rod 2.

In the Peltier effect a direct current passes through a junction of two dissimilar conductors and heat is absorbed or generated at the junction, depending on the direction of current. A number of combinations of dissimilar conductors exhibit the Peltier effect including two different metals, a semi-conductor with a metal, a p-type or n-type semi-conductor with a metal, and a p-type semi-conductor with an n-type semi-conductor. Although all such combinations are capable of exhibiting the Peltier effect, preferably the combination has large thermoelectric power, low thermal conductivity and high electrical conductivity. In addition, the materials should preferably be inexpensive, readily formable and easy to solder and weld.

The hot junctions of the Peltier elements are physically connected, for example by soldering, to a plurality of temperature conductive perforated fins 6. These fins are, for example, sheets of a copper alloy 1/16 of an inch thick having a large number of perforated holes through them. The top and sides of the fins are held within a tube formed by the insulative body 1. On the side of body 1 near the knife end of the handle (side A in FIGURE 1) a blower fan 7 driven by an electrical subminiature motor 8, takes in air through opening 9 and blows that air through the perforated fins 6 within the tube formed by body 1 and out of the air exhaust 10. Blower 9 may be replaced by an external source of pressurized air, for example, a small pressure line connecting the handle to an air pump.

In the smaller handles made in accordance with the present invention, the blower fan 7 may be eliminated and the heat dissipated into the air by the fins physically attached to the hot ends of the Peltier cells.

On the side of the handle opposite the blower (side B in FIGURE 1) a temperature sensitive device 11 is in physical contact with rod 2. This temperature device includes an electrical thermocouple or thermistor which is inserted in a cavity in rod 2 so as to touch the sides of the cavity. Temperature sensitive device 11 is electrically connected to a temperature control dial 12 on the side B of the surgical handle. Dial 12 electrically controls the amount of power flowing to the Peltier cells 3, for example by means of an electric potentiometer. Dial 12 and the temperature sensing device 11 are part of an electrical circuit which functions so that a temperature dialed on dial 12 will be automatically maintained. Similar controls are widely known and are used in automatic blankets and other devices in which a predetermined temperature is maintained by regulating an electric current.

The direct current to the Peltier cells 3 and motor 8 is supplied from bridge rectifier 50 (see FIG. 4). Alternating current is supplied bridge 50 through wires 13 which are connected to transformer 14. The primary of transformer 14 is connected to A.C. current source 15. The full-wave rectifying bridge 50 changes the A.C. current from the secondary of transformer 14 into D.C. current for operation of the Peltier cells.

Other electrical sources may be envisioned for use with the surgical knife of the present invention. For example, a small battery may be inserted in the end of the knife or the power may be derived from a plurality of silicon solar cells on the face of the handle.

On the side of the handle (side A of FIGURE 1) a male handle end is provided in the end of rod 2 to permit insertion of a plurality of different surgical instruments. In the embodiment of FIGURE 1 the tip (male end) of the handle comprises a spring button lock 16 and two screw groove guides 17. This end enables the surgical [instruments] *tools* to be screwed onto the end of the handle held firmly during use and to be readily unfastened.

FIGURE 2 shows a variation of the spring button lock and the screw groove guide which may be utilized with the cooled handle of FIGURE 1. In FIGURE 2 a triangular slot or cavity 18 is cut within rod 2 and a male cone 19 positioned at the bottom of the cavity.

Figure 8:
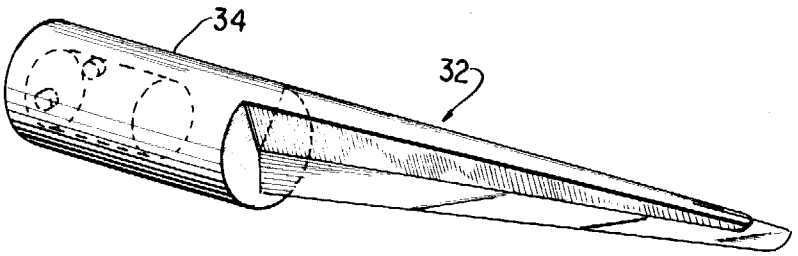
FIGURE 8 is a perspective view of a surgical knife with its handle portion adapted to fit into the male end shown in FIGURE 1.
Figure 6:
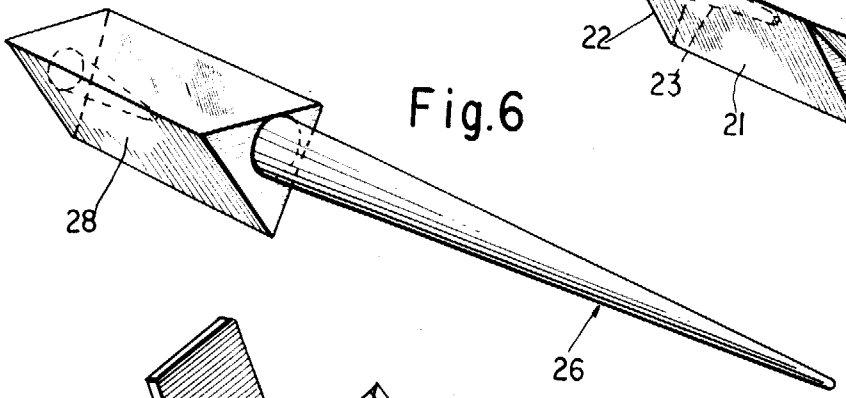
FIGURE 6 is a surgical probe with its handle portion adapted to fit into the male end of FIGURE 2.
Figure 7:
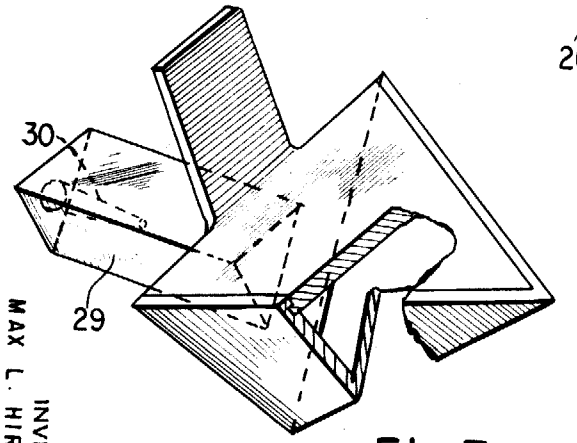
FIGURE 7 is a perspective view of a triangular biopsy scoop with its handle portion adapted to fit into the male end shown in FIGURE 2.

FIGURES 5–8 illustrate various surgical [instruments] *tools* which may be utilized with the cooling handle of the present invention. These surgical [instruments] *tools* are all made of good temperature (heat) conductive material, for example, copper alloy, and their cutting edges are preferably of a hard sharpenable material such as high carbon steel. In the blade 20 (FIGURE 5) the handle portion 21 has a triangular external configuration 22 so as to fit within cavity 18. A female bore 23 is cut in the end of the handle portion 21 to fit over male cone 19. The blade 20 has a cutting edge 24 of high carbon steel. The probe 26 (FIGURE 6) is of good temperature (heat) conductive copper alloy. Preferably portions of the probe are covered with a heat insulative plastic material. The external configuration of the handle end of the probe 28 is triangular and has a female bore portion. In the triangular biopsy probe 29 (FIGURE 7) the handle portion 30 is triangular and has an internal female bore.

In the surgical blade 32 (FIGURE 8) the body of the material is of a copper alloy and the cutting edge is of high carbon steel. The handle of blade 32 comprises a metal rod 34 having two protruding screw tips on its inside surface. The spring button lock 16 of the male end of the handle of FIGURE 1 has a small hole which snaps over the protruding tips. In all cases, there is a good physical contact between the rod 2 and the surgical instruments, so as to permit the cooling temperature to be readily transferred.

The primary usefulness of the blade is in operations upon parenchymal surgery, which is accompanied by capillary bleeding, for example in brain, kidney and liver operations.

In minor surgery, pain is minimized by the local anesthesia produced by the instrument, the area kept dry by vasoconstriction, and the tissue maintained in its cellular vitality.

I claim:

1. A surgical instrument comprising a heat conductive [body having a knife edge in heat conductive relation with the body,] *surgical tool*, a heat conductive rod heat conductively connected to said [body,] *tool*, a plurality of Peltier cells each having a cold and a hot junction connected at their cold junction to the rod, means to connect the Peltier cells to a source of direct current electricity, heat radiating metal fins connected to the hot junctions of the Peltier cells, and a thermally and electrically insulative handle [comprising the exterior portion of the instrument whereby the knife edge is] *surrounding the Peltier cells and a portion of the rod whereby the surgical tool is* cooled for surgical operations.

2. A surgical instrument as in claim 1 and also including means to blow cooling air over the fins.

3. A surgical instrument as in claim 2 wherein the blowing means is an electric motor having a shaft and a fan connected to the shaft and wherein the fins are enclosed in a tube having an entrance portion for the entry of the blown air and an exhaust port.

4. A surgical instrument as in claim 1 in which the heat conductive metals are copper alloys.

5. A surgical instrument as in claim 1 and also including a temperature sensitive electrical instrument and a power control device connected together in a circuit and operatively associated with the surgical instrument to provide automatic temperature control for the surgical instrument.

[6. A surgical instrument as in claim 1 in which the source of direct current is an electrical battery in the handle.]

7. A surgical instrument as in claim 1 wherein the heat conductive connection includes means for removably connecting the rod to the [body] *tool*.

8. A surgical instrument as in claim 1 wherein a substantial portion of the surface of said heat conductive [body] *tool* is covered with a heat insulative plastic material. [and the surface of the knife edge portion of said body is heat conductive.]

References Cited

The following references, cited by the Examiner, are of record in the patented file of this patent or the original patent.

UNITED STATES PATENTS

| | | | |
|---|---|---|---|
| 2,746,264 | 5/1956 | Keyes | 62—293 |
| 2,984,077 | 5/1961 | Gaskill | 62—3 |
| 3,088,288 | 5/1963 | Elving | 128—400 X |

RICHARD A. GAUDET, *Primary Examiner.*

W. E. KAMM, *Assistant Examiner.*